United States Patent [19]
Hirose et al.

[11] Patent Number: 5,449,342
[45] Date of Patent: Sep. 12, 1995

[54] APPARATUS FOR ASSISTING BLOOD CIRCULATION

[75] Inventors: Teruo Hirose, Tokyo; Takashi Kawabata, Hasuda, both of Japan

[73] Assignee: Nippon Zeon Co., Ltd., Tokyo, Japan

[21] Appl. No.: 171,359

[22] Filed: Dec. 23, 1993

Related U.S. Application Data

[63] Continuation-in-part of Ser. No. 953,170, Sep. 29, 1992, abandoned.

[30] Foreign Application Priority Data

Sep. 30, 1991 [JP] Japan .................................. 3-278282

[51] Int. Cl.⁶ ...................... A61M 37/00; A61N 1/362
[52] U.S. Cl. ........................................... 604/4; 600/16
[58] Field of Search ............. 128/DIG. 3; 600/16–18; 604/4, 8, 105; 623/3

[56] References Cited

U.S. PATENT DOCUMENTS

| | | | |
|---|---|---|---|
| 4,210,409 | 7/1980 | Child | 128/DIG. 3 X |
| 4,459,977 | 7/1984 | Pizon et al. | 600/17 |
| 4,781,682 | 11/1988 | Patel | 604/105 |
| 4,787,882 | 11/1988 | Clarén | 604/4 |
| 4,808,158 | 2/1989 | Kreuzer et al. | 128/DIG. 3 |
| 5,011,468 | 4/1991 | Lundquist et al. | 600/18 |
| 5,011,469 | 4/1991 | Buckberg et al. | 604/4 |
| 5,147,281 | 9/1992 | Thornton et al. | 600/16 |
| 5,308,319 | 5/1994 | Ide et al. | 600/18 |

*Primary Examiner*—C. Fred Rosenbaum
*Assistant Examiner*—Frank Wilkens, III
*Attorney, Agent, or Firm*—Millen, White, Zelano & Branigan

[57] ABSTRACT

An apparatus for assisting blood circulation includes an inflow tube which can be inserted into the right atrium from a peripheral blood vessel or which can be inserted into the left atrium from a peripheral blood vessel through the right atrium and the foramen ovale of the interarterial septum. An outflow tube is inserted into the aorta or into the carotid artery from a peripheral blood vessel to deliver the blood to the aorta or to the carotid artery. The outlet tube has an outlet for blood on the side of a upstream part of the tube and a blood pump which can take in the blood from the inflow tube and send out the blood to the outflow tube. When the former inflow tube is used, it also comprises an oxygen gas exchanger which exchanges carbon dioxide in the blood for oxygen. The apparatus can be very easily applied to the patient without thoracotomy to assist the circulation of blood. The function of the lung is assisted, the load on the heart is reduced and the blood flow volume of the coronary artery is increased. The circulation of blood in the whole body or in the brain is assisted.

18 Claims, 5 Drawing Sheets

APPARATUS FOR ASSISTING BLOOD CIRCULATION

CROSS-REFERENCE TO RELATED APPLICATION

This is a continuation-in-part of application Ser. No. 07/953,170, filed Sep. 29, 1992, now abandoned.

BACKGROUND OF THE INVENTION

1. Field of the Invention

The present invention relates to a novel apparatus for assisting blood circulation. More particularly, it relates to an apparatus for assisting blood circulation which can circulate blood by inserting an inflow tube and an outflow tube into the body from a peripheral blood vessel with low invasion without thoracotomy to reduce load on the heart.

2. Description of the Prior Art

Auxiliary artificial hearts and full artificial hearts have been widely studied for curing heavy heart diseases and some auxiliary artificial hearts have already been commercialized.

However, application of these technology requires thoracotomy under the full scale and thorough preparation and are practically powerless for saving lives of patients in a sudden emergency like those in acute cardiac insufficiency.

For saving lives of patients in a sudden emergency as described above, assistant blood circulating methods are used for assisting and replacing the pumping function of the heart temporarily with a mechanical method and for recovering the function of the heart.

Counter pulsation method is one of the methods of assistant blood circulating methods, in which blood pressure of aorta is decreased during the systole to decrease the load of the heart and to support the blood flow from the ventricle while it is increased during the diastole to increase the blood flow volume of coronary artery. Thus, this method tries to improve the circulation in the whole body by assisting the function of the malfunctioning ventricle. As the counter pulsation method, the In Aorta Balloon Pumping (IABP) method in which a balloon catheter is inserted into aorta is most generally practiced.

However, the in aorta counter pulsation method has a problem that the effect of the treatment on the whole body is not exhibited much though the load on the heart is reduced and the blood flow volume in the coronary artery is enhanced.

The artery vein bypassing method is used in combination with a membrane oxygen exchange apparatus for the purpose of assisting circulation in the whole body. In the artery vein bypassing method, blood is drawn from an artery and the blood drawn is delivered to a vein by a pump.

These methods all have a problem that the assistance of the circulation in the whole body and the reduction of the load on the heart are not achieved simultaneously.

SUMMARY OF THE INVENTION

The present invention accordingly has an object to provide an apparatus for assisting circulation of blood with low invasion by which the load on the heart can be reduced and the blood circulation in the whole body or in the brain can be assisted.

Extensive investigations undertaken by the present inventors with the object described above lead to a discovery that the object can be achieved without thoracotomy by the method that blood is drawn from the right atrium through an inflow tube inserted to the right atrium from a peripheral blood vessel and the drawn blood is transferred to an outflow tube by a pump after passing through an oxygen exchanger and then delivered to the aorta or to the carotid artery through the outflow tube inserted to the aorta or to the carotid artery from a peripheral blood vessel. The present invention has been completed on the basis of the discovery.

Thus, the present invention comprises the following two inventions.

(1) An apparatus for assisting blood circulation comprising an inflow tube which can be inserted to the right atrium from a peripheral blood vessel to draw blood from the right atrium, an outflow tube which can be inserted to the aorta or to the carotid artery from a peripheral blood vessel to deliver the blood to the aorta or to the carotid artery and has an upstream outlet of blood spaced from a tip of the outflow tube by a selected distance a blood pump which can take in the blood from the inflow tube and send out the blood to the outflow tube and an oxygen gas exchanger which can exchange carbon dioxide in the blood with oxygen.

(2) An apparatus for assisting blood circulation comprising an inflow tube which can be inserted to the left atrium from a peripheral blood vessel through the right atrium and the foramen ovale of the interarterial septum to draw blood from the left atrium, an outflow tube which can be inserted to the aorta or to the carotid artery from a peripheral blood vessel to deliver the blood to the aorta or to the carotid artery and has an upstream outlet for blood spaced from a tip of the outflow tube by a selected distance and a blood pump which can take in the blood from the inflow tube and send out the blood to the outflow tube.

Other and further objects, features and advantages of the invention will appear more fully from the following description.

BRIEF DESCRIPTION OF THE DRAWINGS

The invention will be described with reference to the accompanying drawings, wherein.

The numbers in the figures have the meanings as listed in the following:
1: an inflow tube
2: an inlet to take in blood
3: a spiral
4: a balloon
5: a connector
6: a balloon connector
7: a marecot
8: an outflow tube
9: an opening to send out blood
10: a balloon
11: an outlet of blood
12: a balloon connector
13: a penetration core
14: a guide wire
15: a penetration core
16: under great vein
17: upper great vein
18: right atrium
19: foramen ovale
20: right ventricle
21: left atrium
22: pulmonary artery
23: left ventricle
24: aorta
25: femoral vein
26: femoral artery

DETAILED DESCRIPTION OF THE INVENTION

The invention is explained in detail in the following.

In the invention, it is necessary that the inflow tube and the outflow tube can be inserted from a peripheral blood vessel.

The peripheral blood vessel for inserting the inflow tube and the outflow tube is preferably a blood vessel located close to skin and having a larger diameter and more preferably the femoral vein, the iliac vein, the carotid vein, the subclavian vein, the femoral artery, the iliac artery, the carotid artery and the subclavian artery. Because the method of the invention utilizes the inflow tube and the outflow tube which can be inserted from a blood vessel located close to skin, it can draw and deliver blood very easily without thoracotomy, or without making a large cut to the body. The insertion of the inflow tube and the outflow tube may be made transcutaneously or surgically by exposing the blood vessel. It is preferable that the operations of insertion of the inflow tube and the outflow tube are made while the operation is watched by the radioscopy.

The kind of the inflow tube is not particularly limited but various kinds of tube can be utilized so long as it has the function of taking in blood from the blood vessel. It is preferable that the tube has an opening for taking in blood at the tip of the tube. It is also preferable that the inflow tube is inserted from a peripheral vein.

It is necessary that the inflow tube has an outer diameter suitable for inserting into a blood vessel and least disturbing the blood flow in the blood vessel. A tube having an outer diameter in the range from 5 to 20 mm is generally utilized. The preferable inner diameter of the inflow tube is varied depending on the flow volume of the blood to be assisted and a tube having diameter in the range from 4 to 18 mm is generally utilized.

The inflow tube is required to have a length sufficient for reaching the right atrium or the left atrium after being inserted from a peripheral blood vessel, which is generally in the range from 70 to 100 cm.

The kind of the outflow tube is not particularly limited but various kinds of tubes can be utilized so long as it has the function of sending out blood to a blood vessel and has an outlet of blood on the side of the upstream part of the tube.

The location of the outlet of blood is not particularly limited so long as it is at the upstream of the tube but the location in the range from 5 to 60 cm from the tip of the tube is generally preferable. It is also preferable that the outflow tube has another opening for sending out blood at the tip of the tube in addition to the outlet through the side of the upstream part of the tube.

The outlet of blood on the side of the upstream part of the tube has a mechanism for adjusting the blood flow volume. Examples of the mechanism for adjusting the blood flow volume are a valve, an orifice and the like other mechanisms.

It is preferable that an opening of the outlet of blood through the side of the upstream part of the outflow tube can be controlled so that the blood flow volume from the outlet satisfies the equation:

$$0.1 \leq F_p/(F_d+F_p) \leq 0.5$$

wherein $F_d$ is the blood flow volume leaving the tip of the outflow tube into the aorta and $F_p$ is the blood flow volume expelled from an outlet through the side out of the outflow tube at an upstream location on the outflow tube into the blood vessel. The upstream location is disposed proximate the branching point of the aorta a femoral artery.

When the value described above is less than 0.1, the blood becomes harder to flow and the blood flow in the lower limbs tends to be hindered, occasionally leading to necrosis. When the value is more than 0.5, it becomes difficult to send out sufficient blood from the outlet at the tip of the tube.

Control of the blood flow volume in the preferred range can be made by suitably selecting the strength and structure of a valve, an orifice or the like.

It is further preferable that an inner tube is inserted to the inside of the side of the upstream part of the outflow tube so that the outlet on the side of the upstream part of the outflow tube can be closed during the insertion of the outflow tube. During the insertion of the outflow tube, there is a possibility that blood is blown out of the outlet by a high blood pressure. The possibility of blown out blood can definitely be removed by closing the outlet of blood by inserting the inner tube to the outlet from the inside.

It is also preferred that a balloon is attached to the outflow tube and the outflow tube is provided with the function of the In Aorta Balloon Pumping (IABP). When the outflow tube is attached with the balloon, it is preferable that the outside is covered with a peel-off type sheath because of easier operation of insertion. The outflow tube is inserted into the blood vessel while it is covered with the sheath and the sheath is removed by peeling off after the tube is inserted.

It is necessary that the outflow tube has an outer diameter suitable for inserting into a blood vessel and least disturbing the blood flow in the blood vessel. A tube having the outer diameter in the range from 4 to 15 mm is generally utilized. The preferable inner diameter of the inflow tube is varied depending on the flow volume of the blood to be assisted. Because the outflow tube having a smaller inner diameter than the inflow tube can deliver blood of the same flow volume, a tube having diameter in the range from 3 to 13 mm is generally utilized. When a vibration blood pump is utilized as the blood pump, a tube having an inner diameter in the range from 2 to 10 mm can also be utilized.

The outflow tube is required to have a length sufficient for reaching the right atrium or the left atrium after being inserted from a peripheral blood vessel, which is generally in the range from 30 to 120 cm.

For the purpose of removing bubbles during the insertion of the tube, a branch or a cock may be attached to the inflow tube and the outflow tube at a suitable part outside of the body.

The inflow tube and the outflow tube of the invention preferably have a connector for connection with the blood pump or the oxygen gas exchanger.

When the inflow tube and the outflow tube of the invention are inserted into a peripheral blood vessel transcutaneously, the inflow tube and the outflow tube preferably have a hemostatic attachment so that blood does not flow out through the interface of the inflow tube or the outflow tube and the blood vessel. Examples of the hemostatic attachment are hemostatic sheath and the like.

Material utilized for the inflow tube and the outflow tube of the invention is not particularly limited but various kinds of material such as the material used for the cardiac cannulae can be utilized. Examples of such material are plasticized polyvinyl chloride, silicone, polyethylene, polypropylene, polyurethane and the like. A softer material is more preferable. The inflow tube of the invention is preferably reinforced in spiral form with a linear material, such as metals and rigid resins.

The inner surface of the inflow tube and the outflow tube in contact with blood preferably has the antithrombosis property so that the tubes can be utilized continuously for a long time. Thus, it is preferable that the tubes are composed of an antithrombosis material, such as polyurethane, cardiothane and the like or that the tubes are treated with an antithrombosis treatment, such as fixed application or gradual release of an antithrombosis material like heparin, urokinase, h-TPA and the like.

The inflow tube and the outflow tube of the invention is preferably coated or mixed with a radiopaque material.

In the invention, the blood pump which takes in blood from the inflow tube and send out the blood to the outflow tube is essential.

As the blood pump, various kinds of pump can be utilized, such as pulse type pumps like a diaphragm pump, a sack pump, a tubular pump, a pusherplate pump and the like, vibration pumps like a vibration pump of a permanent magnet type and the like, roller pumps, centrifugal pumps and the like other pumps. Preferable pumps among them are vibration pumps which have an excellent effect on blood circulation to peripheral blood vessels even when the outflow tube is rather narrow. It is also preferred that the in aorta balloon pumping function is provided to the outflow tube so that the effects of the reduction of the load on the heart and the increase of blood flow volume in the coronary artery are further enhanced.

The blood pump of the invention is attached to the outside of the body and the apparatus of the invention can be quickly applied to a patient in emergency.

The invention comprises the invention (1) in which the inflow tube is inserted to the right atrium and the invention (2) in which the inflow tube is inserted to the left atrium. The invention (1) is explained first.

In the invention (1), an inflow tube which can be inserted to the right atrium from a peripheral blood vessel is necessary.

In the invention (1), when the outflow tube is inserted to the aorta, the outflow tube can be directly inserted to the aorta from a peripheral artery or inserted to the aorta from a peripheral vein through the right atrium, the foramen ovale of the interarterial septum and the left atrium. When the latter route to the right atrium is used for both of the inflow tube and the outflow tube, it is preferable that the inflow tube and the outflow tube are made into a double tube made with an outer tube and an inner tube because of easier operation, though the two kinds of tubes may be inserted separately from the peripheral blood vessel.

When the inflow tube and the outflow tubes are made into a double tube, either the outer tube or the inner tube may be utilized as the inflow tube. However, it is rather preferable that the outer tube is utilized as the inflow tube because, in this structure, the outer tube utilized as the inflow tube is shorter than the inner tube utilized as the outflow tube and blood can be drawn out from the right atrium. The far end of the inner tube utilized as the outflow tube is composed of a single tube with no outer tube attached and inserted into the left atrium through the foramen ovale of the interarterial septum.

When the outflow tube is inserted to the carotid artery, it is preferable that the tube is directly inserted to the carotid artery.

When the outflow tube is inserted to the aorta through the foramen ovale and the left atrium, it is preferred that the outflow tube is attached with a penetration core. The outflow tube can easily pass through the foramen ovale by the attached penetration core. The tip of the penetration core has a suitable curvature, facilitating the penetration through the foramen ovale. The foramen ovale is the part open during a fetus and closed after the birth and the penetration through it makes no damage to the heart, thus the method of penetration through the foramen ovale being shown to be an excellent method. The penetration core is composed of a soft material and takes approximately linear form when it passes through blood vessels so that it does not make any problem to the insertion of the outflow tube. A combination of the outflow tube and the penetration core made by one shot molding may be utilized.

It is preferred that the penetration core penetrates the foramen ovale by inserting a penetration needle through a hole of a guide wire which are equipped at the inside of the penetrating core. This method still more facilitates the penetration of the foramen ovale.

When the outflow tube is inserted into the left atrium through the foramen ovale, the tube preferably has a device to prevent the detachment of the inserted tube from the foramen ovale. Various kinds of devices, such as a balloon and a marecot, can be utilized for this purpose.

In the invention (1), an oxygen gas exchanger which can exchange carbon dioxide in blood with oxygen is essential. The oxygen gas exchanger is placed before or after the blood pump in the apparatus.

As the oxygen gas exchanger, various kinds of oxygen gas exchanger can be utilized and membrane oxygen gas exchangers are preferable among them. When the oxygen gas exchanger is operated while blood is vibrated by the vibration pump, the efficiency of the oxygen gas exchange is enhanced and this is an advantageous practice.

When an outflow tube which can be inserted from a peripheral blood vessel to the fight ventricle or to the pulmonary artery is utilized in place of the outflow tube described above and the blood drawn from the right atrium is transferred to the outflow tube inserted to the right ventricle or to the pulmonary artery with a pump after passing through the oxygen gas exchanger, the assistance of the lung or the assistance of the lung and the right ventricle can be made. For this operation, it is preferred that the inflow tube and the outflow tube are made into a double tube, though the operation can be made by inserting the two kinds of tube separately from a peripheral blood vessel.

In the invention (2), an inflow tube which can be inserted from a peripheral blood vessel to the left atrium through the large vein, the right atrium and the foramen ovale is necessary.

The inflow tube preferably has a penetration core at the tip. The inflow tube can easily penetrate the foramen ovale by making use of the penetration core. The tip of the penetration core is shaped with a suitable curvature to facilitate the penetration of the penetration core through the foramen ovale. The shape at the tip of the penetration core is not particularly limited but a shape of an arc of 1/10 to ¼ is generally utilized. It is preferred that the penetration core has such a structure that can pass through the inside of the inflow tube like the penetration core in the invention (1) and can be freely pushed out from or pulled back into the inside of the inflow tube. The penetration core is composed of a soft material and takes approximately linear form when it passes through blood vessels so that it does not make any problem to the insertion of the inflow tube.

It is preferred that the penetration core penetrates the foramen ovale by inserting a penetration needle through a hole of a guide wire which are equipped at the inside of the penetration core. This method still more facilitates the penetration of the foramen ovale. A combination of the penetration core and the penetration needle made by one shot molding is preferred because the penetration needle is not easily detached from the penetration core.

It is preferred that the inflow tube has a device to prevent the detachment of the inserted tube from the foramen ovale. Various kinds of devices, such as a balloon and a marecot, can be utilized for this purpose.

In the invention (2), when the inflow tube is inserted into the right atrium, the tube may be inserted from a peripheral blood vessel while the penetration core is attached to the inside of the tube or, alternatively, the tube alone may be inserted from the peripheral blood vessel to the right atrium at first, then the penetration core being inserted to the inside of the tube. A balloon is preferably attached to the tip of the inflow tube when the tube is inserted from a peripheral blood vessel because inflation of the balloon to a suitable degree helps the tube reach the right atrium easily along the blood stream.

In the invention (2), an oxygen gas exchanger is not essential. However, the utilization of it is not precluded.

According to the method of the invention, blood is drawn out by utilizing the inflow tube which can be inserted from a peripheral blood vessel to the right atrium and the drawn blood is sent into the aorta or the carotid artery after the exchange of oxygen gas by utilizing the outflow tube which can be inserted from a peripheral blood vessel to the aorta or the carotid artery. Thus, it is made possible that the function of the lung is assisted, the load on the heart is reduced and the circulation to the whole body or to the brain is assisted.

Also according to the method of invention, blood is drawn out by utilizing the inflow tube which can be inserted from a peripheral blood vessel to the left atrium through the fight atrium and foramen ovale of the interarterial septum and delivered to the aorta or to the carotid artery. Thus, it is made possible that the load on the heart is reduced and the circulation to the whole body or to the brain is assisted.

DESCRIPTION OF THE PREFERRED EMBODIMENTS

The invention will be understood more readily with reference to the following examples and drawings; however, these examples are intended to illustrate the invention and are not to be construed to limit the scope of the invention.

Figure 1:
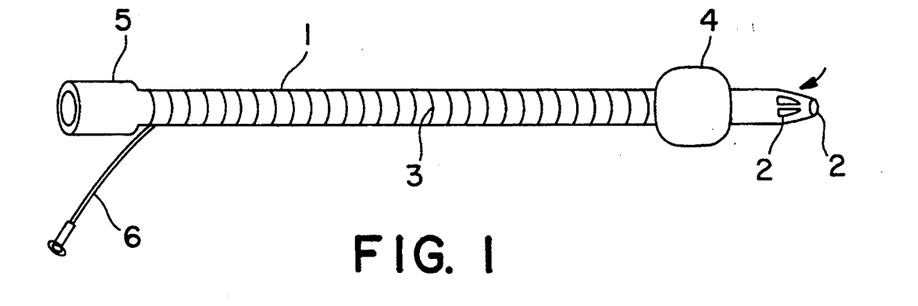
FIG. 1 is a perspective view showing an example of the inflow tube of the invention.

FIG. 1 is a perspective view showing an example of the inflow tube of the invention.

The inflow tube has a structure comprising a main influo tube 1 made of polyurethane and having an outer diameter of 8 mm and an inner diameter of 7 mm and a nylon spiral 3 wound around it for reinforcement. An inlet for blood 2 is made at the tip of the inflow tube 1 for taking in blood. A balloon 4 is attached at the tip of the inflow tube 1. The balloon 4 is connected to a balloon connector 6 and can be inflated or deflated by charging or discharging helium through the balloon connector 6. When the balloon 4 is inflated after the inflow tube 1 is inserted through the foramen ovale of the interarterial septum, the inflow tube is prevented from detaching from the foramen ovale. A connector 5 to the pump is attached to the base end of the inflow tube 1.

Figure 2:
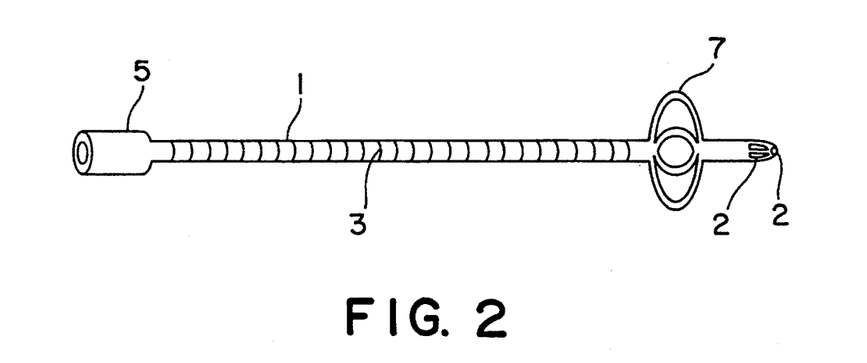
FIG. 2 is a perspective view showing another example of the inflow tube of the invention.

FIG. 2 is a perspective view showing another example of the inflow tube of the invention.

In this example, a marecot 7 is attached to the inflow tube in place of the balloon 4 in the preceding example. The marecot 7 takes the form shown in FIG. 2 when no external force is applied and, when an external force is applied to extend the inflow tube 1, it loses the protrusions by being extended to the direction of the tube 1.

Figure 3:
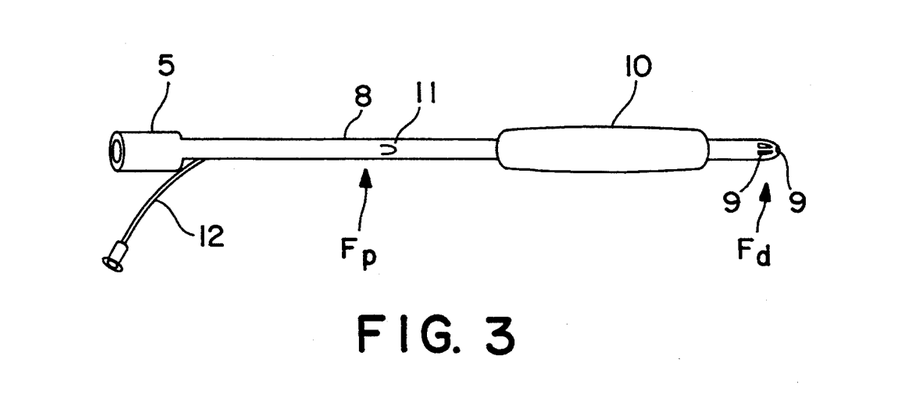
FIG. 3 is a perspective view showing an example of the outflow tube of the invention.

FIG. 3 is a perspective view showing an example of the outflow tube of the invention.

At the tip of the outflow tube 8 made of polyurethane and having an outer diameter of 7 mm and an inner diameter of 6 mm, an opening for sending out blood is made: A balloon 10 is attached at a short distance from the tip. The balloon 10 is connected to a balloon connector 12 having an outer diameter of 2 mm and can be inflated or deflated by charging or discharging helium gas through the balloon connector 12. The balloon 10 is the balloon utilized for the counter pulsation and can deliver blood to the whole parts of the body with pulses. A flap valve 11 is attached to the side of the tube at an upstream location and before the baloon 10. All these components constitute the outlet of blood 11.

Figure 4:
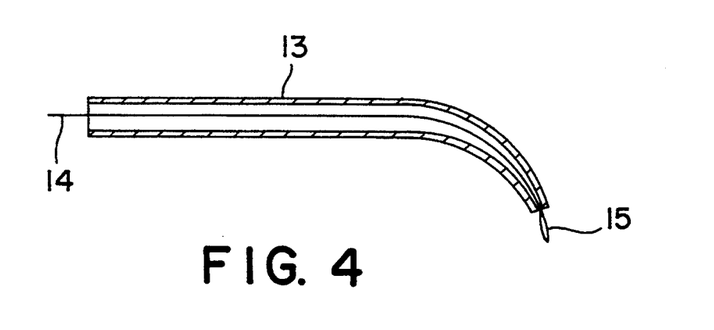
FIG. 4 is a sectional view showing an example of the penetrating core of the invention.

FIG. 4 is a sectional view showing an example of the penetration core of the invention.

The tip of the penetration core 13 has a shape with a curvature so that it can easily penetrate the foramen ovale. A guide wire 14 is inserted to the the inside of the penetration core 13 and, at the tip of the guide wire, a penetration needle 15 is attached to facilitate the penetration through the foramen ovale. The guide wire 14 moves along the inside of the penetration core 13 and can place the penetration needle 15 at the tip of the penetration core 13.

Figure 5:
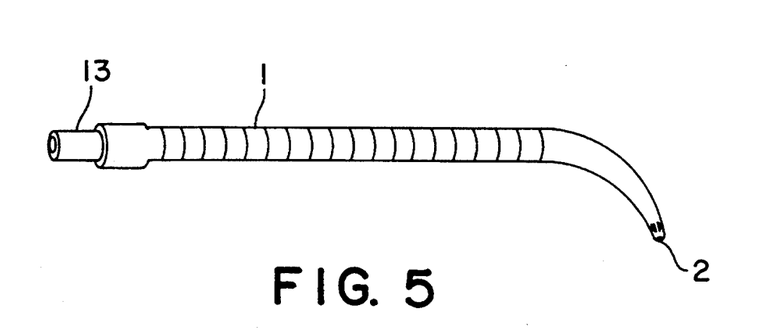
FIG. 5 is a perspective view showing a structure in which a penetrating core 13 is inserted into the inflow tube 1 of the invention.

FIG. 5 is a perspective view showing a structure in which a penetration core 13 is inserted into the inflow tube 1 of the invention.

The penetration core 13 can move along the inside of the inflow tube 1 and is inserted to the tip the inflow tube 1. The inflow tube 1 takes the shape with a curvature in accordance with the shape of the penetration core 13.

Figure 6:
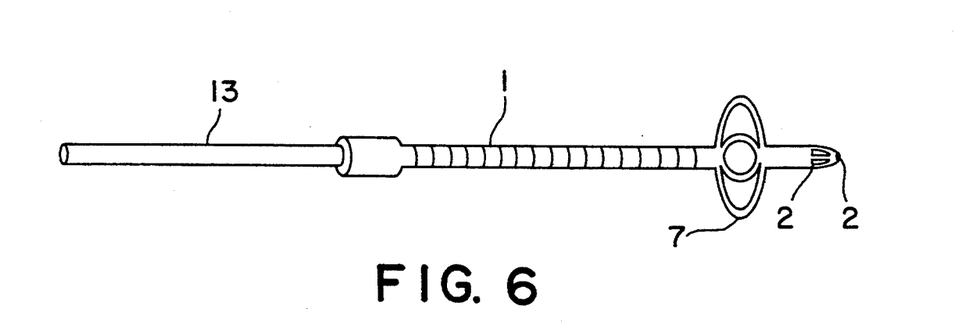
FIG. 6 is a perspective view showing a structure in which the penetrating core 13 shown in FIG. 5 is pushed out of the inflow tube 1.

FIG. 6 is a perspective view showing a structure in which the penetration core 13 shown in FIG. 5 is pushed out of the inflow tube 1.

Because the penetration core 13 is pushed out of the inflow tube 1, the marecot 7 is protruded to the direction perpendicular to the axis of the inflow tube I at the tip of the tube 1.

Figure 7:
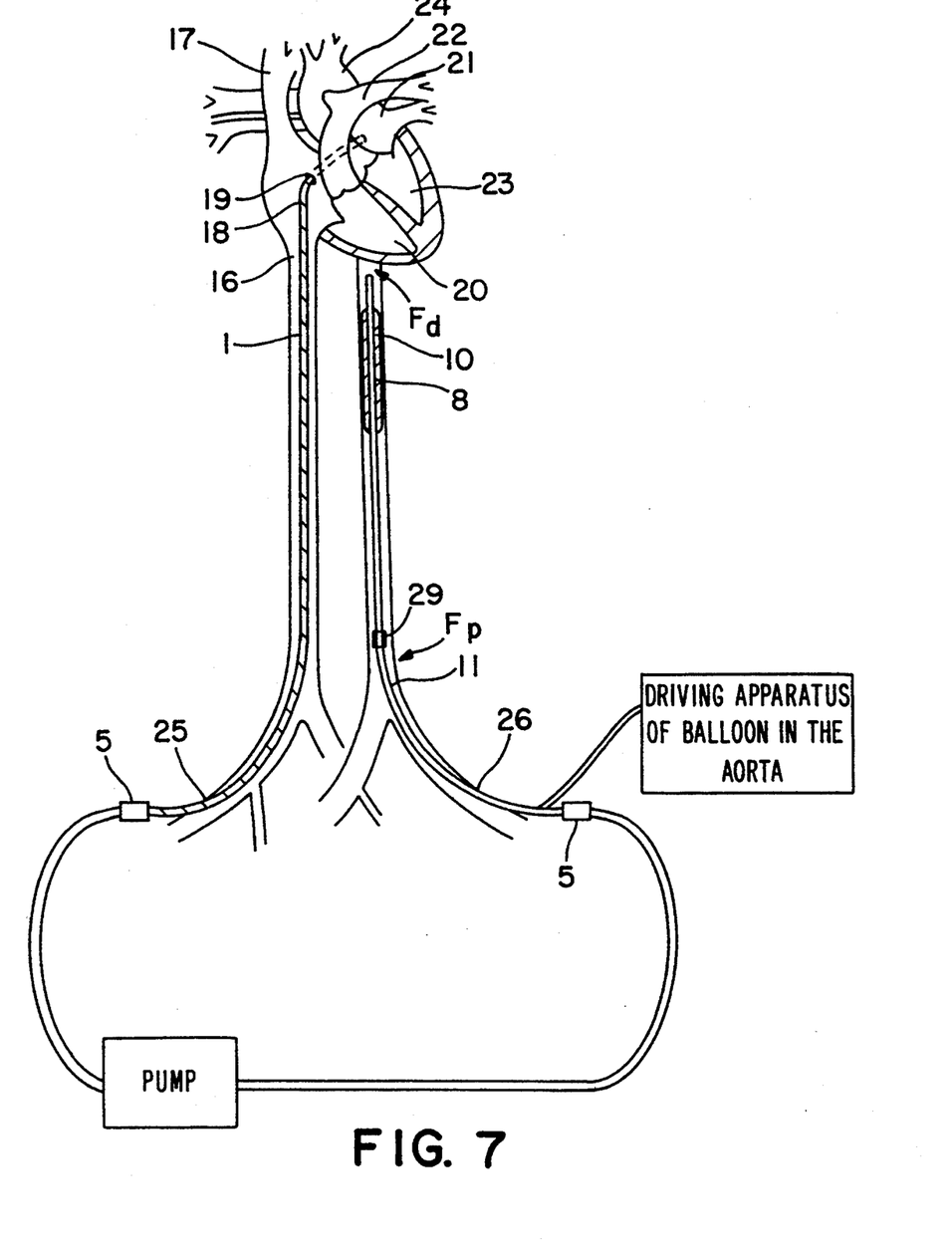
FIG. 7 shows outline of the apparatus for assisting blood circulation of the invention 2 applied to the body.

FIG. 7 shows outline of the apparatus for assisting blood circulation of the invention 2 applied to the body.

The inflow tube I is inserted in the body from the femoral vein 25 to the left atrium 21 through the under large vein 16, the fight atrium 18 and the foramen ovale 19. The outflow tube 8 is inserted from the femoral artery 26 to the aorta 24. The blood taken in by the inflow tube 1 is delivered to the aorta by the outflow tube 8 through the vibration blood pump. The blood is delivered in a synchronized action with the pulse of the heart so that the delivery of blood makes no load on the heart. It is preferred that the inflation and deflation of the balloon 10 is synchronized with the pulse of the heart by utilizing a driving apparatus which can synchronize the movement with the pulse of the heart. The outlet of blood 11 made at the upstream location of the outflow tube 8 is placed at the branching point of the aorta and the femoral artery. The flow volume of the blood from the outlet 11 of the outflow tube was 20% of the total flow volume of blood.

An orifice or valve 29 is positioned in the outlet tube 8, downstream of the flap 11 at the upstream location. The orifice or valve 29 adjusts the blood flow volume to select the values of the aforementioned parameters $F_p$ and $F_d$ so that the expression $0.1 < F_p/(F_d + F_p) < 0.5$ is satisfied.

Appropriate control means are well known in the art and are disclosed in the patent literature. For example, U.S. Pat. No. 4,210,409 to Child, incorporated herein by reference, describes a pump and control at column 2, line 22, through column 3, line 2, and U.S. Pat. No. 5,147,281 to Thornton, incorporated herein by reference, discloses a biological fluid pumping arrangement in columns 3 and 4 and describes a control circuit for controlling operation of a pump at column 7, lines 24–35.

A balloon is not shown attached to the tip of the inflow tube 1 shown in FIG. 7. However, when a balloon is attached, detachment of the inflow tube from the foramen ovale can be prevented by inflating the balloon after the tube attached with the balloon has been inserted into the 1 left atrium.

Figure 8:
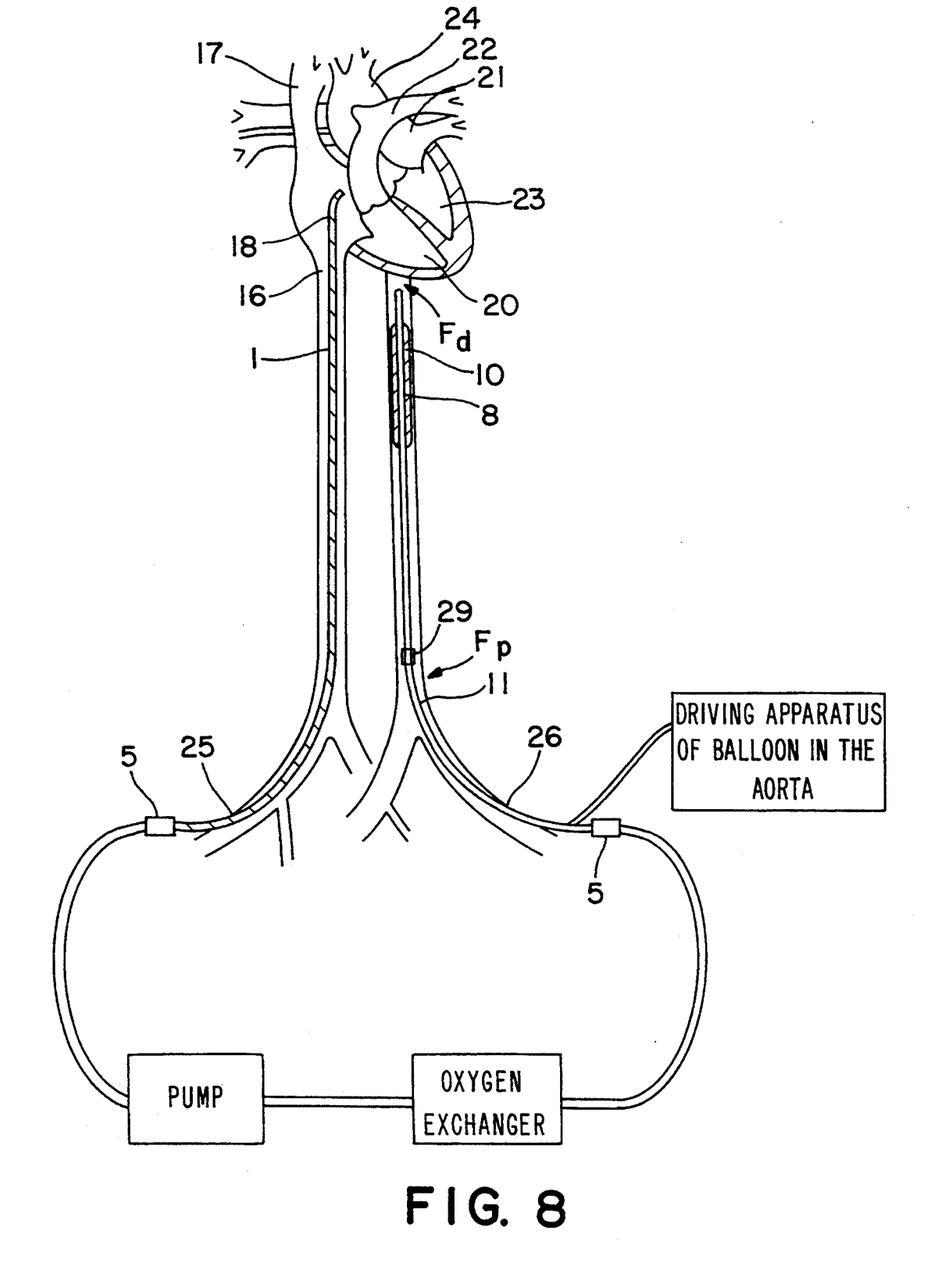
FIG. 8 shows outline of the apparatus for assisting blood circulation of the invention 1 applied to the body.

FIG. 8 shows outline of the apparatus for assisting blood circulation of the invention 1 applied to the body.

The inflow tube 1 is inserted in the body from the femoral vein 25 into the right atrium 18 through the under large vein 16. The outflow tube 8 is inserted from the femoral artery 26 to the aorta 24. The blood taken in by the inflow tube 1 is delivered to the aorta through the vibration blood pump and the oxygen exchanger. Other features in FIG. 8 are the same as in FIG. 7.

The oxygen exchange is placed after the vibration blood pump in FIG. 8, but the order may be reversed.

Figure 9:
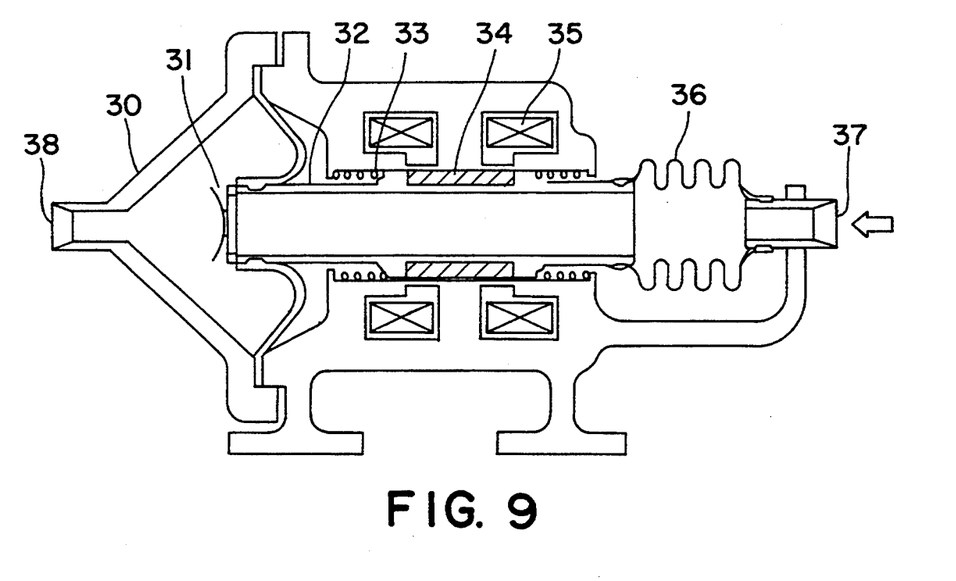
FIG. 9 is a sectional view of a vibration pump utilized in the apparatus for assisting blood circulation of the invention.

FIG. 9 is a sectional view of a vibration blood pump of the two stage permanent magnet type utilized in the apparatus for assisting blood circulation of the invention.

The vibration pump performs the pumping function by vibration of a tube to the axial direction of the tube.

A vibrating tube 32 is supported by a supporting spring 33 from the both sides and a vibrating valve is attached at an end of the tube. The tube is vibrated to the axial direction of tube by the magnetic force. The vibrating force is generated by varying the bias magnetic field generated by a permanent magnet 34 at the circumference of the vibrating tube 32 by the action of magnetic field of an electromagnetic coil 35. Amplitude and frequency of the vibration of the vibrating tube can be controlled by strength and frequency of electric current through the coil. The sliding part of the blood pump is sealed against fluid by bellows 36 and rubber film to prevent destruction of blood.

Blood is sucked in at the inlet 37. By increase of blood pressure by the action of the vibration of the vibrating tube 32, the spring valve is opened and the blood in the vibration tube is transferred to the space of the spring valve (the casing 30). When the pressure in the vibration tube is reduced, the valve is closed and the blood in the space of the spring valve is discharge from the outlet 38 by the piston effect of the leftward movement of the vibrating tube 32.

While the invention has been particularly shown and described with reference to preferred embodiments thereof, it will be understood by those skilled in the art that the foregoing and other changes in form and details can be made therein without departing from the spirit and scope of the invention.

To summarize the advantages obtained by the invention, the apparatus for assisting blood circulation of the invention can be very easily applied to the patient without thoracotomy to assist the circulation of blood.

When the inflow tube of the invention is inserted to the fight atrium to draw out blood and the outflow tube of the invention is inserted to the aorta or to the carotid artery to send back the blood, the assistance of the lung, the reduction of load of the heart, the increase of blood flow volume of the coronary artery and the assistance of the circulation of the whole body or of the brain can be made.

When the inflow tube of the invention is inserted to the left atrium to draw out blood and the outflow tube of the invention is inserted to the aorta or to the carotid art m- ]to send back the blood, the reduction of load of the heart, the increase of blood flow volume of the coronary artery and the assistance of the circulation of the whole body or of the brain can be made.

What is claimed is:

1. An apparatus for assisting blood circulation in a human comprising an inflow tube for insertion into the right atrium of the heart of the human from a peripheral blood vessel of the human to draw blood from the right atrium, an outflow tube having a tip for insertion into either the aorta or the carotid artery of the human from a peripheral blood vessel of the human to deliver the blood to the aorta or to the carotid artery, the outflow tube further having two outlets for blood therefrom, one at the tip of the outflow tube and the other through the side of the outflow tube at an upstream location of the outflow tube spaced from the tip by a selected distance of 5 to 60 centimeters sufficient to cause blood from the upstream location to flow into the femoral artery, a blood pump for pulling blood from the inflow tube and expelling blood through the outflow tube and an oxygen gas exchanger positioned at a location downstream of the pump for exchanging carbon dioxide in the blood with oxygen and means located in the outflow tube for controlling blood flow volume therethrough wherein the blood flow volume through the outlet satisfies the equation:

$$0.1 \leq F_p/(F_d+F_p) \leq 0.5$$

wherein $F_d$ is the blood flow volume leaving the tip of the outflow tube and $F_p$ is the blood flow volume expelled from the outlet through the side of the outflow tube at the upstream location of the outflow tube.

2. An apparatus for assisting blood circulation as claimed in claim 1 wherein a mechanism for adjusting the blood flow volume is attached to the outlet for blood on the side of a upstream part of the outflow tube.

3. The apparatus of claim 1, wherein the upstream outlet is spaced from the tip of the outflow tube by a distance at least approximately equal to the distance between the tip of the outflow tube and the branching location of the femoral artery and aorta of the specific humans with whom the apparatus is used.

4. An apparatus for assisting blood circulation as claimed in claim 1 wherein an inner tube is inserted at the inside of the upstream part of the outflow tube so that the outlet for blood through the side of the upstream part of the outflow tube can be closed.

5. An apparatus for assisting blood circulation as claimed in claim 1 wherein the blood pump is a vibration blood pump.

6. An apparatus for assisting blood circulation as claimed in claim 1 wherein the inflow tube has a device for preventing detachment.

7. An apparatus for assisting blood circulation as claimed in claim 1 wherein the outflow tube includes a balloon for effecting counter pulsation.

8. The apparatus of claim 1, wherein the upstream outlet is spaced from the tip of the outflow tube by a distance at least approximately equal to the distance between the tip of the outflow tube and the branching location of the femoral artery and aorta of the specific human with whom the apparatus, is used.

9. The apparatus of claim 1, wherein only a single inflow catheter is disposed in the vein and only a single outflow catheter is disposed in the femoral artery and the aorta.

10. An apparatus for assisting blood circulation in a patient comprising an inflow tube for insertion into the left atrium of the patient from a peripheral blood vessel through the right atrium of the patient and the foramen ovale of the interarterial septum of the patient to draw blood from the left atrium, an outflow tube having a tip for insertion into the aorta or carotid artery of the patient from a peripheral blood vessel to deliver the blood to the aorta or to the carotid artery, the outflow tube further having a side wall with an outlet therethrough for blood at an upstream location thereof, the upstream location being spaced from the tip by a selected distance, of 5 to 60 centimeters and a blood pump for taking in blood from the inflow tube and sending blood out of the outflow tube.

11. An apparatus for assisting blood circulation as claimed in claim 10 wherein a mechanism for adjusting the blood flow volume is attached to the outlet for blood on the side of an upstream part of the outflow tube.

12. An apparatus for assisting blood circulation as claimed in claim 10 wherein an opening for the size of the outlet of blood through the side wall of the of the outflow tube at the upstream location is controlled so that blood flow volume through the outlet satisfies the equation:

$$0.1 \leq F_p/(F_d+F_p) \leq 0.5$$

wherein $F_d$ is the blood flow volume leaving the tip of the inflow tube and $F_p$ is the blood flow volume expelled from the outlet through the opening wall thereof.

13. The apparatus of claim 12, wherein the upstream outlet is spaced from the tip of the outflow tube by a distance at least approximately equal to the distance between the tip of the outflow tube and the branching location of the femoral artery and aorta of the specific mammal with which the apparatus is used.

14. An apparatus for assisting blood circulation as claimed in claim 10 wherein an inner tube is inserted at the inside of the upstream part of the outflow tube so that the outlet for blood on the side of the upstream part of the outflow tube can be closed.

15. An apparatus for assisting blood circulation as claimed in claim 10 wherein the blood pump is a vibration blood pump.

16. An apparatus for assisting blood circulation as claimed in claim 10 wherein the inflow tube has a device for preventing detachment.

17. An apparatus for assisting blood circulation as claimed in claim 10 wherein the outflow tube includes a balloon for effecting counter pulsation.

18. The apparatus of claim 10, wherein only a single inflow catheter is disposed in the vein and only a single outflow catheter is disposed in the femoral artery and the aorta.

* * * * *